(12) United States Patent
Behiels et al.

(10) Patent No.: US 7,826,682 B2
(45) Date of Patent: Nov. 2, 2010

(54) METHOD OF SUPPRESSING A PERIODICAL PATTERN IN AN IMAGE

(75) Inventors: Gert Behiels, Edegem (BE); Pieter Vuylsteke, Mortsel (BE)

(73) Assignee: Agfa HealthCare, Mortsel (BE)

( * ) Notice: Subject to any disclaimer, the term of this patent is extended or adjusted under 35 U.S.C. 154(b) by 1013 days.

(21) Appl. No.: 11/401,693

(22) Filed: Apr. 11, 2006

(65) Prior Publication Data

US 2006/0233453 A1    Oct. 19, 2006

Related U.S. Application Data

(60) Provisional application No. 60/688,930, filed on Jun. 9, 2005.

(30) Foreign Application Priority Data

Apr. 14, 2005  (EP)  ................................. 05102949

(51) Int. Cl.
*G06K 9/40* (2006.01)
*G06K 9/52* (2006.01)
*G06K 9/36* (2006.01)
*G06K 9/00* (2006.01)

(52) U.S. Cl. ........................ 382/275; 382/262; 382/206; 382/280; 382/132; 382/254

(58) Field of Classification Search ................. 382/262, 382/260
See application file for complete search history.

(56) References Cited

U.S. PATENT DOCUMENTS

| | | | | |
|---|---|---|---|---|
| 4,066,881 A * | 1/1978 | Houdard | ...................... | 708/405 |
| 4,654,721 A * | 3/1987 | Goertzel et al. | ............ | 358/3.04 |
| 4,941,185 A * | 7/1990 | Reed | ........................... | 382/267 |
| 5,073,752 A * | 12/1991 | DeMeester et al. | .......... | 324/309 |
| 5,157,741 A * | 10/1992 | Katayama | .................... | 382/254 |
| 5,504,621 A * | 4/1996 | Okayama et al. | ............. | 359/569 |
| 5,553,157 A * | 9/1996 | Bourguignon et al. | ...... | 382/131 |
| 6,151,417 A * | 11/2000 | Florent | ........................ | 382/265 |
| 6,591,234 B1 * | 7/2003 | Chandran et al. | ........... | 704/225 |
| 6,665,350 B1 * | 12/2003 | Bartkowiak | .................. | 375/275 |
| 6,697,507 B1 * | 2/2004 | Chapman | .................... | 382/131 |
| 6,731,824 B2 * | 5/2004 | Russell | ....................... | 382/280 |
| 6,813,529 B2 * | 11/2004 | Hedley | ........................ | 700/94 |
| 7,050,618 B2 * | 5/2006 | Belykh et al. | ................ | 382/132 |

(Continued)

FOREIGN PATENT DOCUMENTS

EP    1 265 194    12/2002

OTHER PUBLICATIONS

European Search Report for EP 05 10 2949 (Sep. 20, 2005).

(Continued)

*Primary Examiner*—Vikkram Bali
*Assistant Examiner*—Michelle Entezari
(74) *Attorney, Agent, or Firm*—Leydig, Voit & Mayer, Ltd.

(57) ABSTRACT

A short-time Goertzel transform is applied to the image signal to transform it into a representation of the spatial frequency component corresponding to the periodic pattern. This representation is processed. Next the inverse of the transformation is computed and the result of the inverse transformation is removed from the image signal.

16 Claims, 13 Drawing Sheets

U.S. PATENT DOCUMENTS

| | | | |
|---|---|---|---|
| 2001/0012407 A1* | 8/2001 | Takeo | 382/260 |
| 2003/0016854 A1 | 1/2003 | Inoue et al. | |
| 2003/0053600 A1* | 3/2003 | Schmitz et al. | 378/210 |
| 2003/0091243 A1* | 5/2003 | Sasada | 382/260 |
| 2004/0127791 A1* | 7/2004 | Mast et al. | 600/438 |
| 2006/0092297 A1* | 5/2006 | Lee et al. | 348/241 |
| 2006/0110047 A1* | 5/2006 | Reissman et al. | 382/218 |

OTHER PUBLICATIONS

Chau et al.; Direct Formulation for the Realization of Discrete Cosine Transform Using Recursive Structure.

* cited by examiner

METHOD OF SUPPRESSING A PERIODICAL PATTERN IN AN IMAGE

CROSS-REFERENCE TO RELATED PATENT APPLICATIONS

This application claims the benefit of U.S. Provisional Application No. 60/688,930 filed Jun. 9, 2005, which is incorporated by reference. In addition, this application claims the benefit of European Application No. 05102949.4 filed Apr. 14, 2005, which is also incorporated by reference.

FIELD OF THE INVENTION

The present invention relates to a method for suppression of a periodical pattern with a given frequency. It relates more specifically to suppression of periodical patterns caused by the presence of an anti-scatter grid in X-ray images.

BACKGROUND OF THE INVENTION

A commonly used technique to reduce the amount of scattered X-rays in computed radiography, digital radiography as well as classical film-based X-ray systems is the use of anti-scatter grids. These grids are lead foil strips, placed apart at a certain distance in a suitable covering.

There exist different types of anti-scatter grids. In parallel grids, the lead foil strips are parallel, while in honeycomb grids the strips are placed in a honeycomb pattern. The grids are stationary or moving. The use of these grids effectively reduces the radiation scattering but occasionally introduces artefacts such as grid lines into the image.

In a moving system, the motion of the grids removes the grid lines in the image. However, in some circumstances e.g. short exposure time or malfunctioning of the system, the artefacts remain in the image.

If the image is formed digitally or converted afterwards to a digital image representation, Moiré artefacts may appear when displaying the image at a certain scale. These low frequent Moiré artefacts are mostly disturbing and should be eliminated. Before displaying the image, the grid lines, if present in the image, should be removed.

It is a goal of the present invention to eliminate of the negative influence of periodic artefacts e.g. moiré artefacts of zoomed images, without removing diagnostic information.

SUMMARY OF THE INVENTION

The above-mentioned aspects are realised by a method as set out in claim 1.

Specific features for preferred embodiments of the invention are set out in the dependent claims.

The present invention provides a method for suppressing periodical variations centred on given frequency in an image in a given direction, parallel to an image axis.

The method provides a technique to apply a non-linear high frequency attenuating filter parallel and perpendicular to the periodical variation.

This non-linear high frequency attenuating filter can be a median filter. This filter ensures that a minimal amount of relevant information is removed from the original image. This filter does not reduce the image quality of the image.

The method allows the removal of periodic patterns for which the frequency of the variation is not exactly known. It performs a short-time Goertzel transform to obtain a suitable representation of the periodic variation. The result of the short-time Goertzel transform can be presented as a real or imaginary part. A non-linear high frequency attenuating filtering process is performed on this representation or a derivative of this representation. After filtering, removing the diagnostic content from the short-time Goertzel transform, the inverse of the transform is computed and the inverse is used to correct the input data.

The embodiments of the methods of the present invention are generally implemented in the form of a computer program product adapted to carry out the method steps of the present invention when run on a computer. The computer program product is commonly stored in a computer readable carrier medium such as a CD-ROM or a DVD. Alternatively the computer program product takes the form of an electric signal and can be communicated to a user through electronic communication.

DETAILED DESCRIPTION OF THE INVENTION

The presence of an anti-scatter grid manifests itself as a periodic disturbance of the input signal. In the method according to the present invention, we assume that the disturbance is of a pure periodic nature.

It is a goal of the method of the present invention to eliminate of the negative influence of periodic artefacts e.g. moiré artefacts of zoomed images, without removing diagnostic information.

Experiments have shown that removal of sinusoidal signals with the main frequency of the periodic disturbance is good enough for this purpose.

Figure 1:
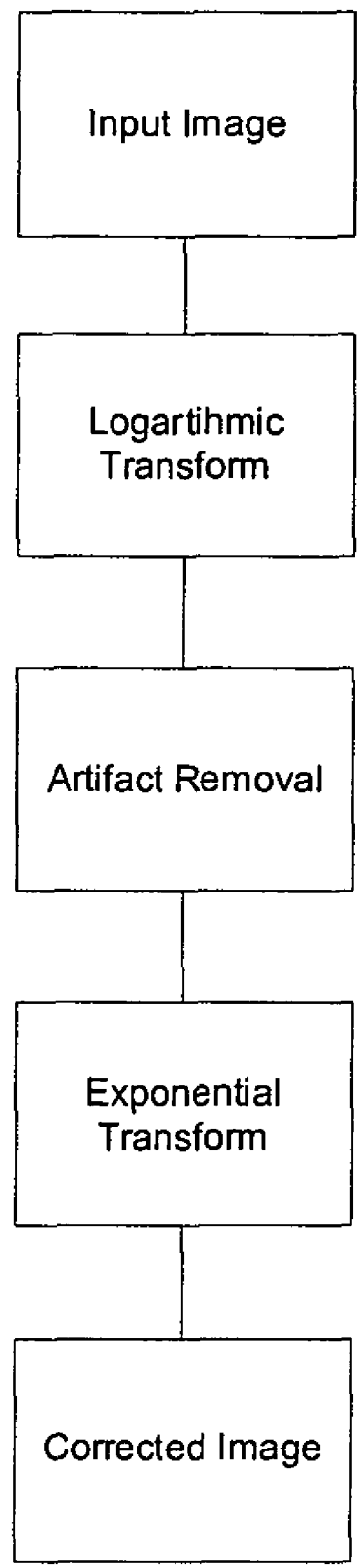
FIG. 1 shows a flowchart for conversion of the multiplicative problem to an additive problem.

The invention can be used to correct periodic artefacts of an additive or multiplicative nature. In the second case, the situation can be converted to artefacts of an additive nature by using a logarithmic transform before processing and an exponential transform after removal of the periodic artefacts (see FIG. 1).

The invention comprises the step of processing the image by applying to the image comprising the artefacts a median or high frequency attenuating filter in the direction of the periodic signal, after estimation/extraction of the periodic artefact, to remove the diagnostic information still present in the periodic signal. Normally such a high frequency attenuating filter removes the periodic information of the signal.

In patent application EP 04 102 185.8 a technique has been described to overcome this problem. This technique only works if the period of the variation is integer.

Because this is not the case for the periodic disturbances of the anti scatter grids, the periodic signal is transformed to a complex representation or amplitude/phase representation of a given frequency.

Such a technique is generally known as the Goertzel transform.

If $s=(s_0, s_1, \ldots, s_N)$ is the input signal, the Goertzel transform for the frequency $\omega$ is defined as $$G(\omega) = \sum_{x=0}^{N} s_x \exp(-i\omega x)$$

$$G(\omega) = \int s(x) e^{-i\omega x} dx.$$

For sake of simplicity, I will only use the integral notation for the formulas. The formulas can be easily converted to our discrete problem. For suppression of the periodical patterns caused by the presence of an anti-scatter grid in X-ray images, the frequency $\omega$ however, is only known to a certain degree of accuracy. Also, because of the nature of the anti scatter grids, this frequency can change a little bit over distance. According to the invention a windowed Goertzel transform, localized in place, is computed. This transform will be called the short-time Goertzel transform $\Gamma$ $$\Gamma(y,\omega) = \int w(x-y) s(x) e^{-i\omega x} dx \qquad \text{Equation 1}$$

The result of Equation 1 for a given frequency $\omega$, is a complex number for each position y. The inverse transform of the complex number is a good estimate of the periodic disturbance.

Figure 2:
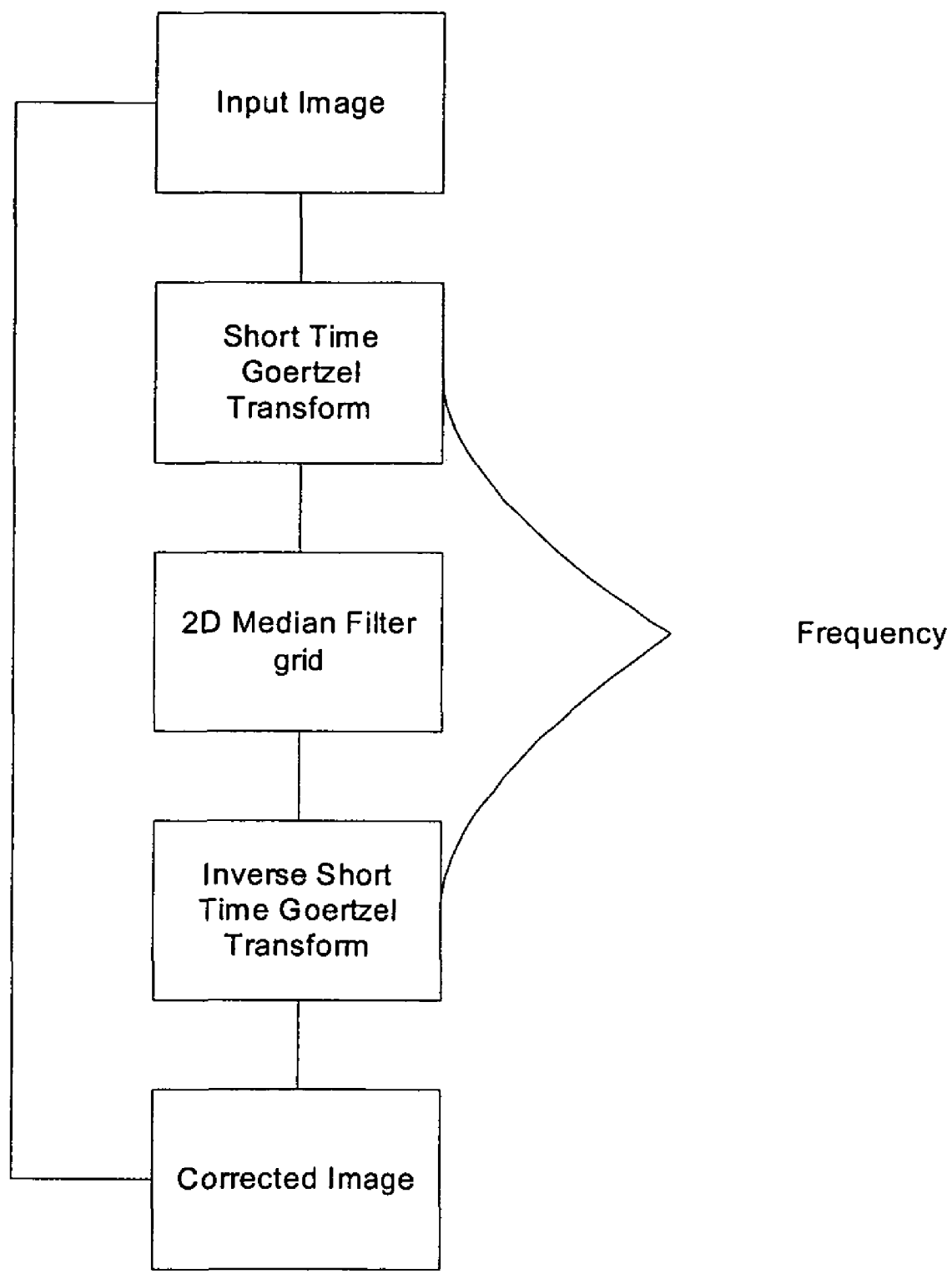
FIG. 2 shows an implementation of the invention with a 2-dimensional median filter.
Figure 3:
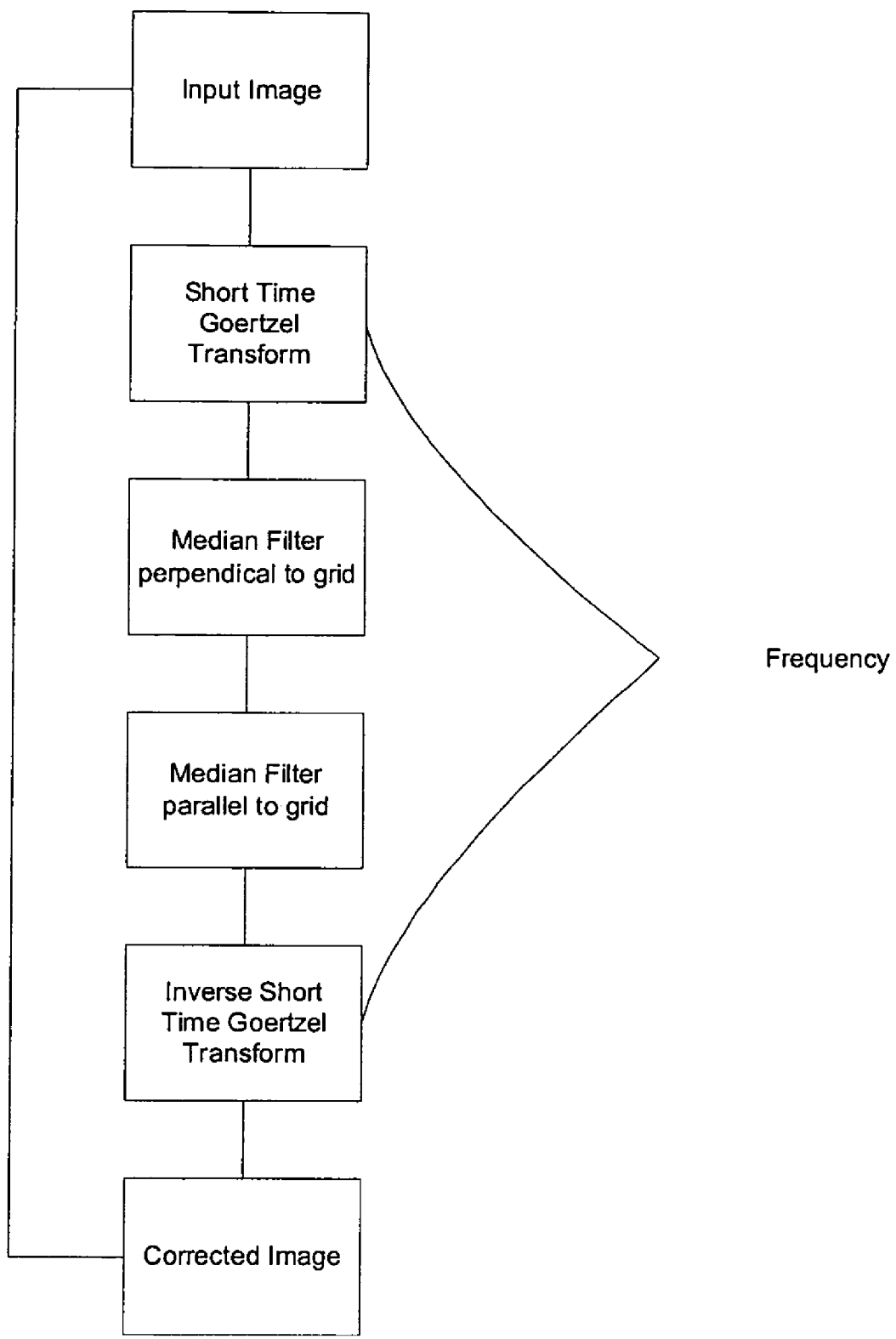
FIG. 3 shows an implementation of the invention with 2 separable median filters.

However, we perform a median or high frequency attenuating filter on this complex representation (or any part or derivative of this representation e.g.: real part, imaginary part, amplitude, phase . . . ). This filter may consist of a 2-dimensional filter, or two separate filters, one parallel to the grid direction and one orthogonal to the grids (see FIG. 2 and FIG. 3).

Figure 4:
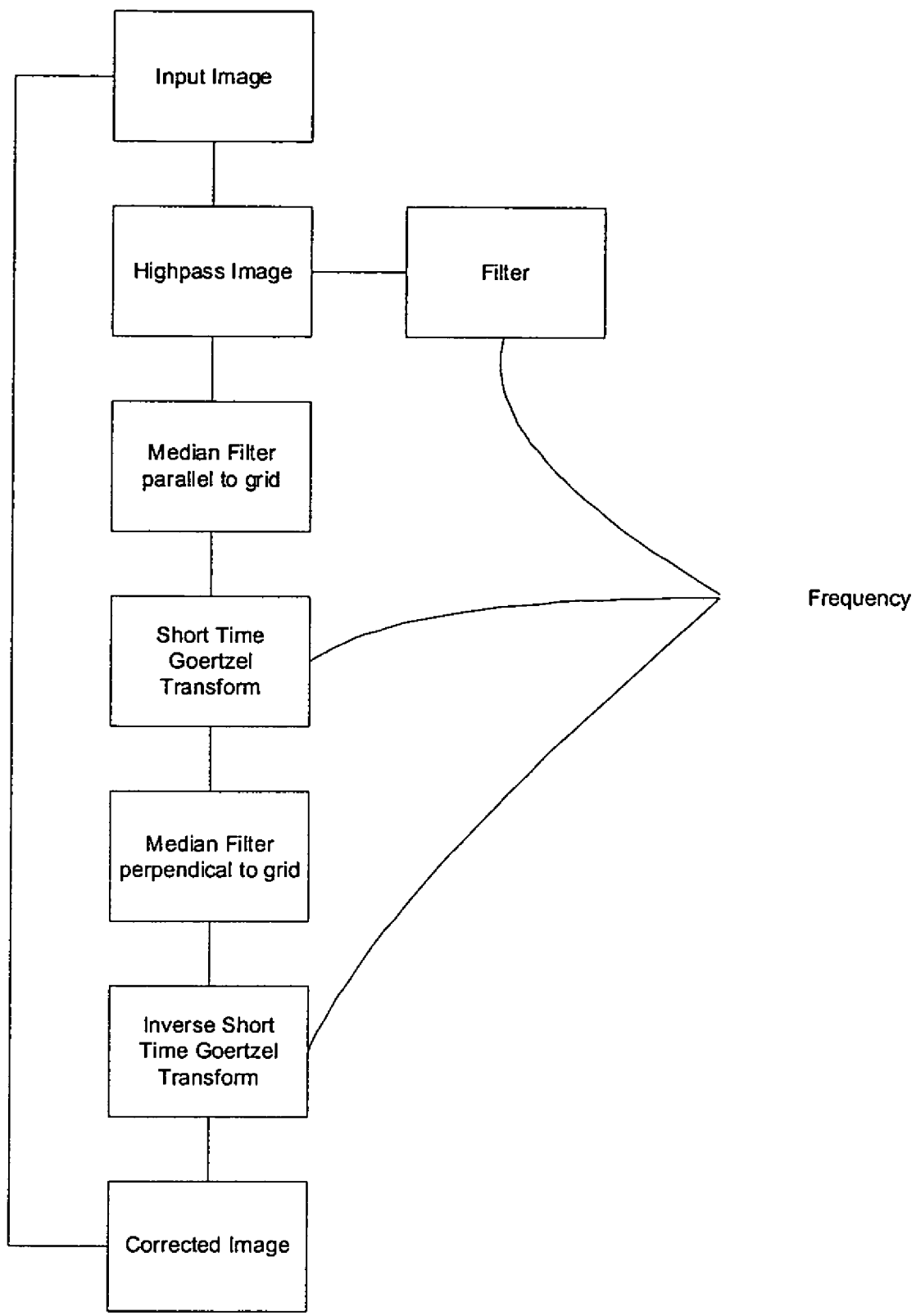
FIG. 4 shows an implementation of the invention with a highpass filter as a preprocessing step.

If we follow a scheme where we already have applied a high frequency attenuating filter parallel to the grids, only a filter orthogonal to the grids is sufficient for robust estimation of the periodic signal (FIG. 4).

If we assume that the input signal s can be defined as $$s(x) = \alpha(x)\cos(\omega x) + \beta(x)\sin(\omega x),$$

which is a reasonable assumption for a model of an antiscatter grid. We want to extract the slowly changing amplitudes $\alpha$, $\beta$ of the grid We divide Equation 1 into the following two parts:

$$\Gamma_c(y,\omega) = \int w(x-y) s(x) \cos(x) dx$$

$$\Gamma_s(y,\omega) = \int w(x-y) s(x) \sin(x) dx$$

Equation 1 transforms to $\Gamma(y,\omega) = \Gamma_c(y,\omega) + i\Gamma_s(y,\omega)$. If we assume that the amplitudes are approximately constant over the extent of our window, we can use the following notations:

$$\Gamma_c(y,\omega) \approx \alpha(y)\Gamma_{cc}(y,\omega) + \beta(y)\Gamma_{cs}(y,\omega)$$

$$\Gamma_s(y,\omega) \approx \alpha(y)\Gamma_{cs}(y,\omega) + \beta(y)\Gamma_{ss}(y,\omega)$$

with $$\Gamma_{cc}(y,\omega) = \int w(x-y) \cos(x) \cos(x) dx$$

$$\Gamma_{cs}(y,\omega) = \int w(x-y) \cos(x) \sin(x) dx$$

$$\Gamma_{scc}(y,\omega) = \int w(x-y) \cos(x) \cos(x) dx$$

With this knowledge, we can approximate the amplitudes $$\alpha(y) = \frac{\Gamma_c(y, \omega)\Gamma_{ss}(y, \omega) + \Gamma_s(y, \omega)\Gamma_{cs}(y, \omega)}{\Gamma_{cc}(y, \omega)\Gamma_{ss}(y, \omega) - \Gamma_{cs}(y, \omega)\Gamma_{cs}(y, \omega)} \qquad \text{Equation 2}$$

$$\beta(y) = \frac{\Gamma_c(y, \omega)\Gamma_{sc}(y, \omega) - \Gamma_s(y, \omega)\Gamma_{cc}(y, \omega)}{\Gamma_{cc}(y, \omega)\Gamma_{ss}(y, \omega) - \Gamma_{cs}(y, \omega)\Gamma_{cs}(y, \omega)}$$

If some postprocessing on the amplitude representation is performed, resulting in the new amplitude representation ($\alpha'$, $\beta'$) the reconstructed signal s' is given by $$s'(x) = \alpha'(x)\cos(\omega x) + \beta'(x\_sin(\omega x))$$

The advantages of this transformation are twofold. Only one spectral component needs to be computed and the transformation generates a slowly varying output, which is ideal for processing before transforming it back to the original input domain.

Figure 5:
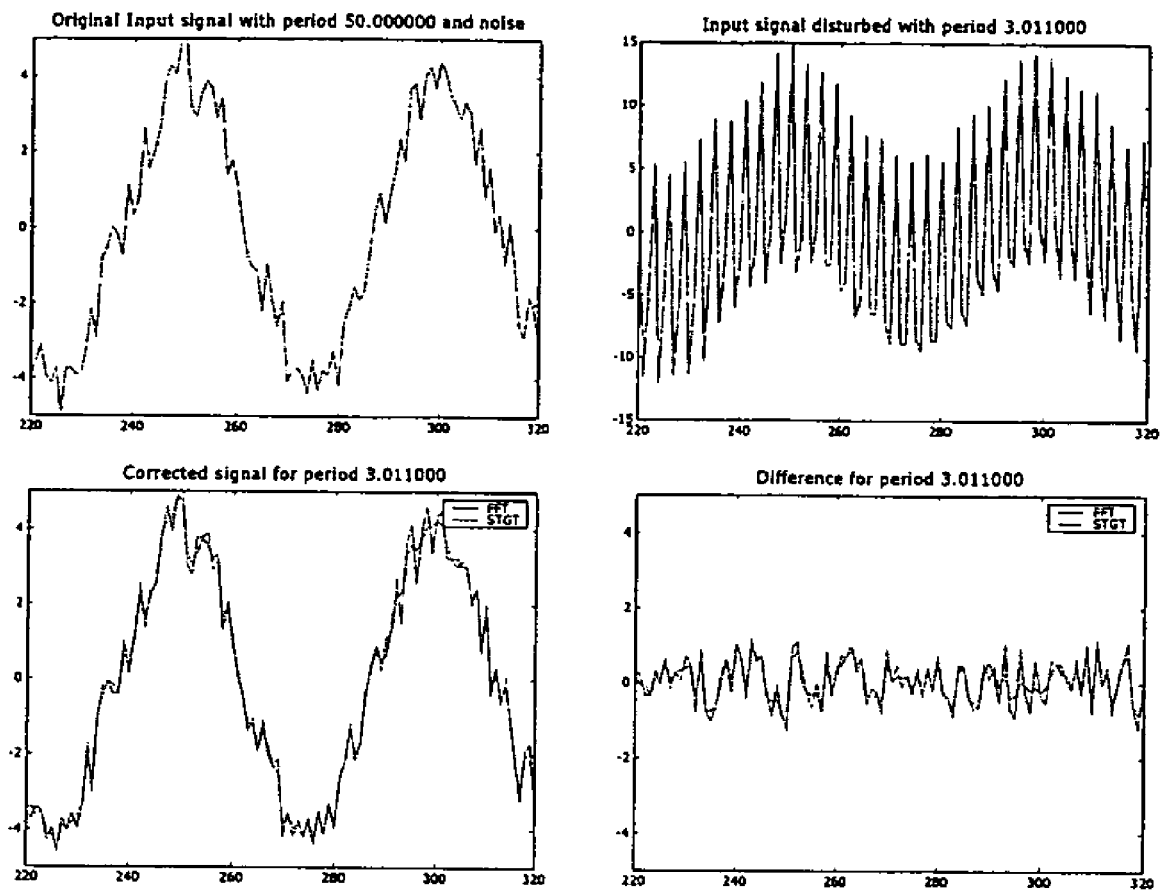
FIG. 5 shows the result of the invention on a computer generated input signal. The result of the invention is compared with the result of a similar technique where 3 spectral components in the Fourier domain are suppressed.
Figure 6:
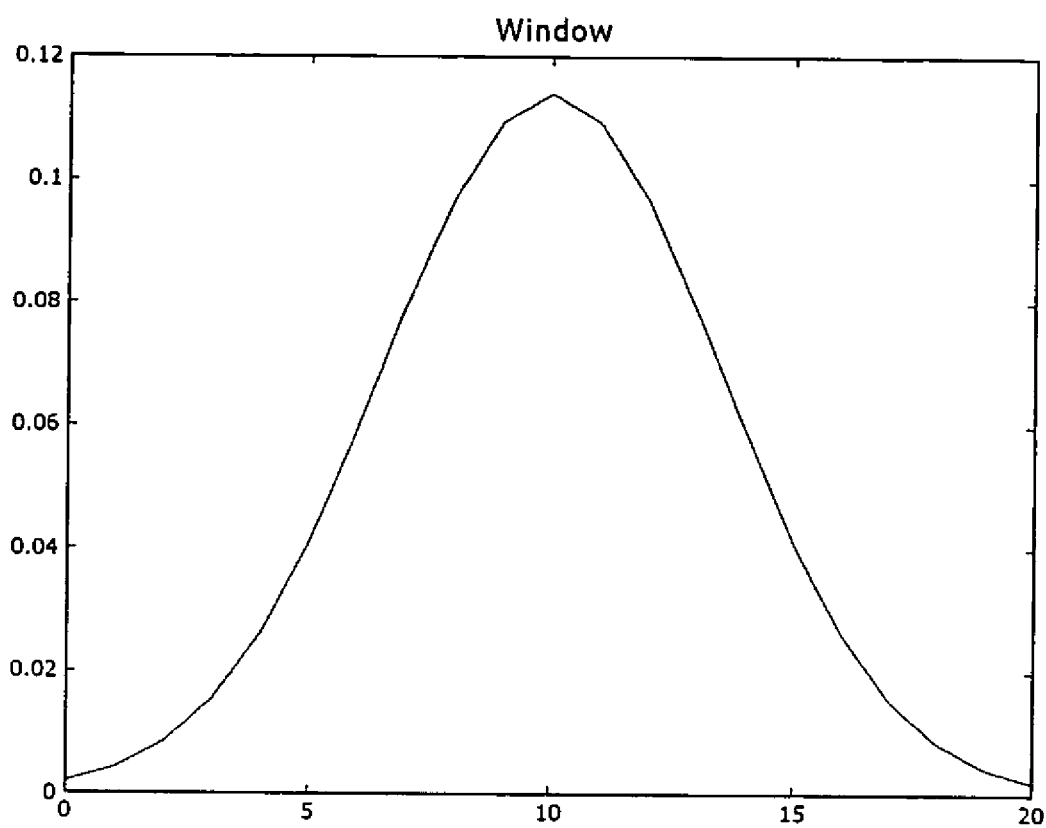
FIG. 6 shows the window that is used to compute the short-time Goertzel transform for a signal with a period of 3.011 that needs to be suppressed (see also FIG. 5)
Figure 7:
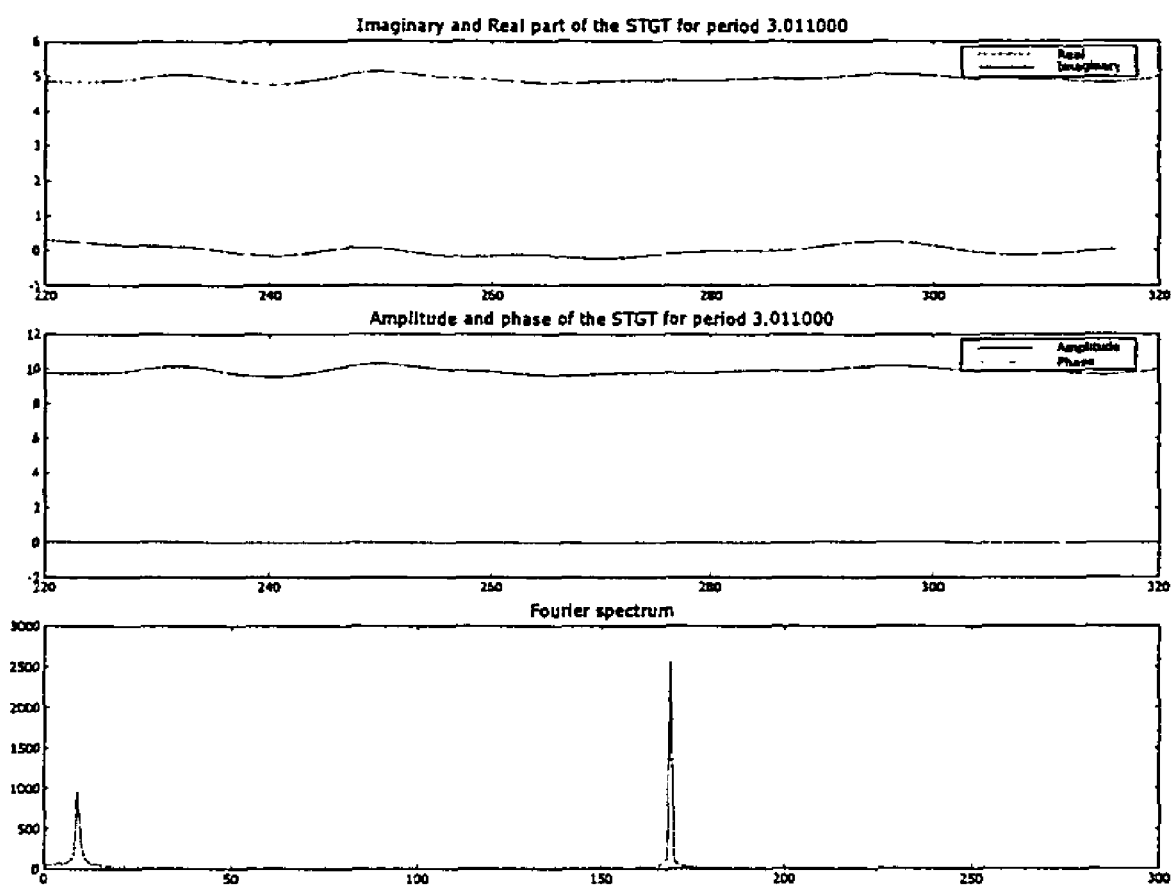
FIG. 7 shows the result of the short-time Goertzel transform of the input signal of FIG. 5.

For an input signal with a period of 50 with a little bit of noise, which is disturbed by a synthetic grid with a period of 3.011 pixels (FIG. 5), we compare our approach with an approach in which 3 spectral components in the Fourier domain are suppressed. The window that is used to compute the short-time Goertzel transform for the frequency $$\omega = \frac{2\pi}{3.011}$$

is displayed in FIG. 6. In FIG. 7 the output of the short-time Goertzel transform is displayed as both parts of the complex notation and as an amplitude-phase notation. Both representations vary smoothly, which makes it easy to apply high frequency attenuating filters to remove remaining diagnostic information. FIG. 7 also displays the Fourier spectrum of the input signal. FIG. 6 illustrates that the result of both methods is comparable.

Figure 8:
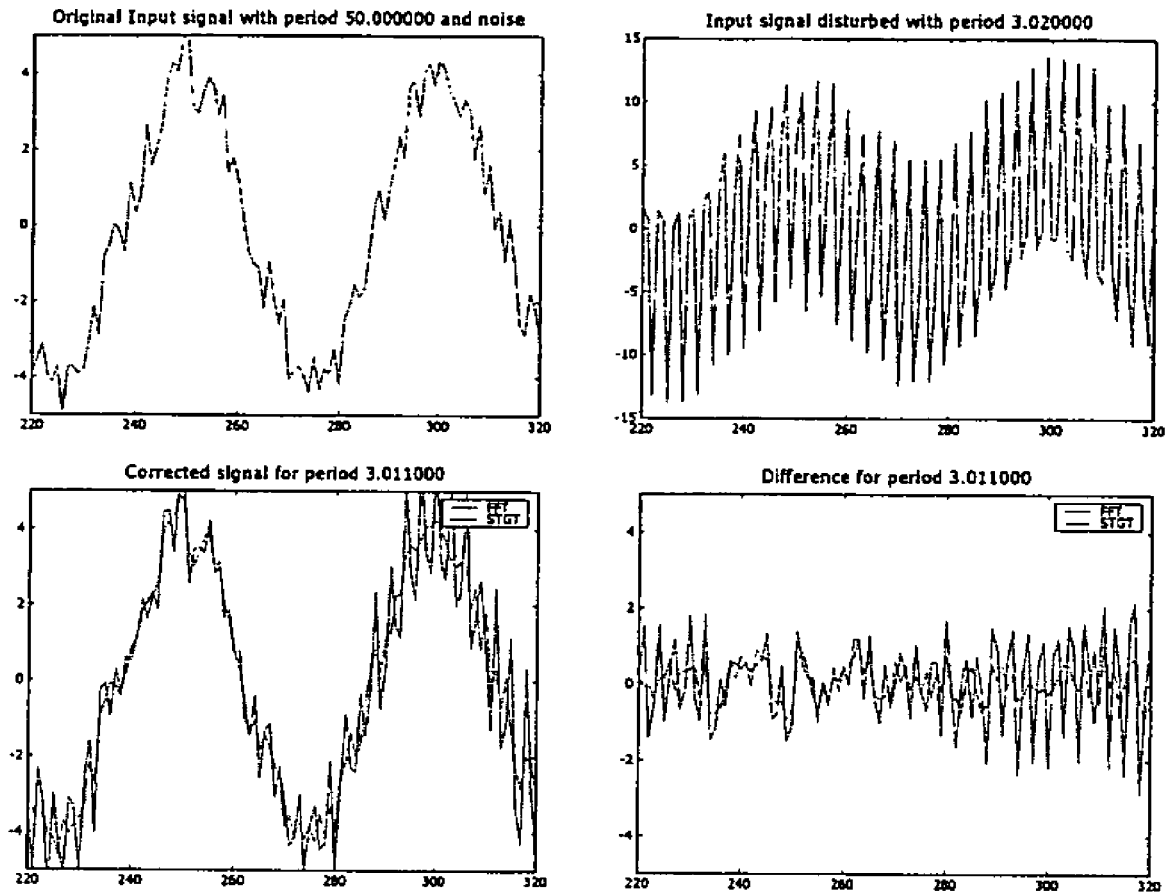
FIG. 8 shows the result of the invention on a computer generated input signal. The result of the invention is compared with the result of a similar technique where 3 spectral components in the Fourier domain are suppressed. In this case, the period of the disturbing signal does not coincide with the central frequency of a spectral component in the Fourier domain.
Figure 9:
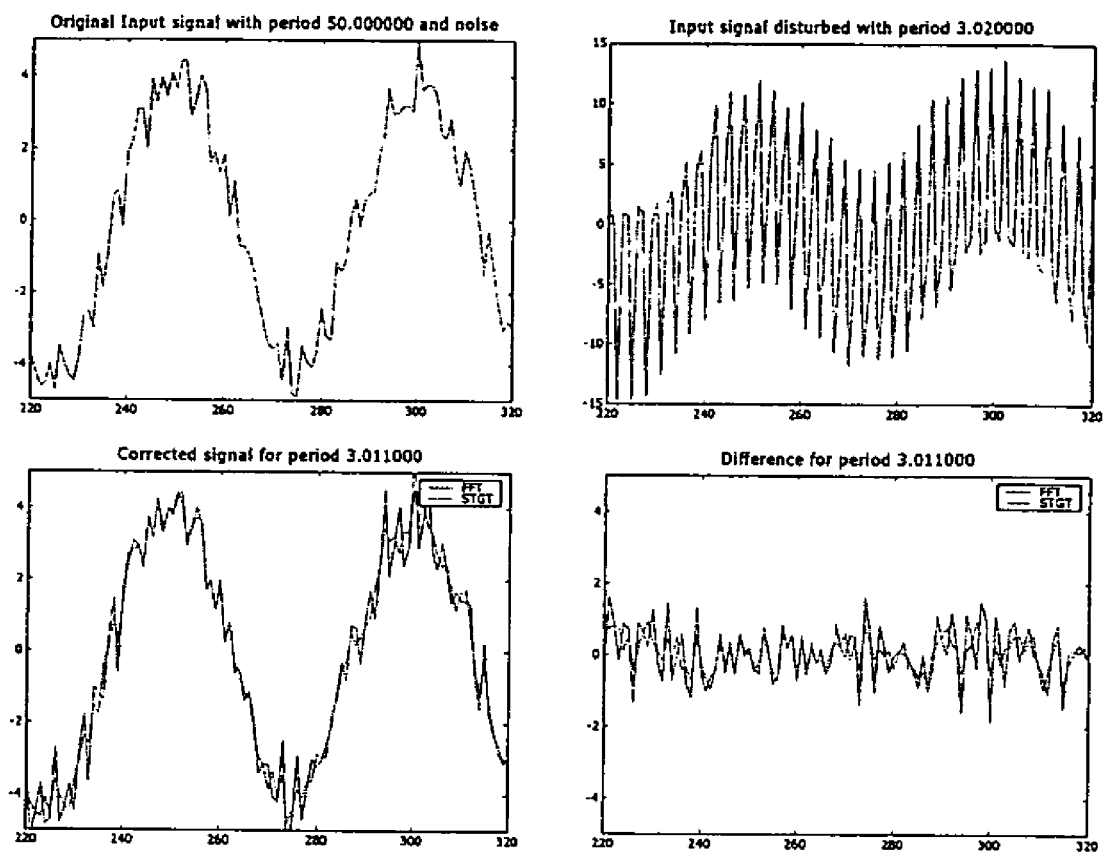
FIG. 9 shows the result of the invention on a computer generated input signal. The result of the invention is compared with the result of a similar technique where 7 spectral components in the Fourier domain are suppressed. In this case, the period of the disturbing signal does not coincide with the central frequency of a spectral component in the Fourier domain.

In the assumption that the period of the signal is not 3.011 but 3.02, the outer limit of the same frequency bin in the Fourier domain, we have different outcomes (see FIG. 8). The short-time Goertzel transform performs better than the Fourier method. We can achieve the same result with the Fourier technique, but than we need to suppress more spectral components. In FIG. 9 seven spectral components are suppressed. This makes the Fourier transform more time consuming.

Figure 10:
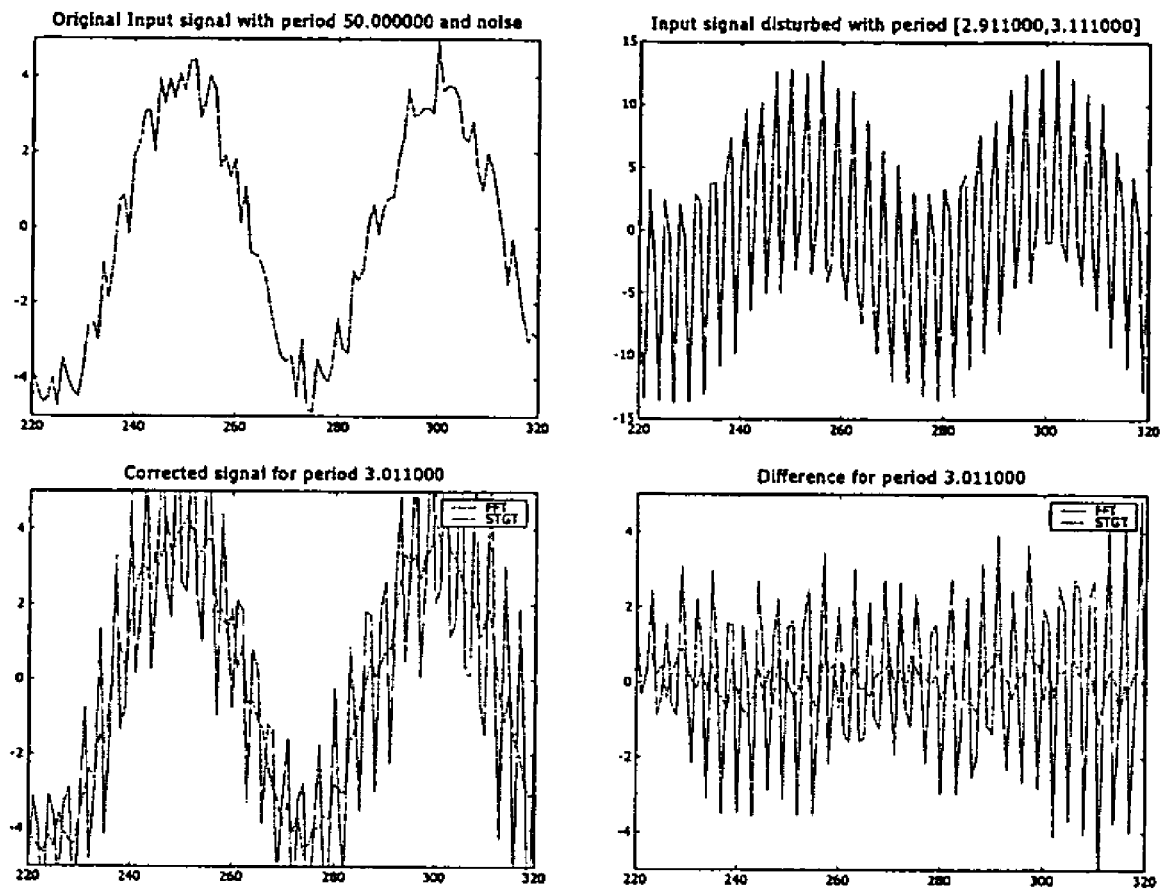
FIG. 10 shows the result of the invention on a computer generated input signal. The result of the invention is compared with the result of a similar technique where 7 spectral components in the Fourier domain are suppressed. In this case, the period of the disturbing signal varies between 2.911 and 3.111.

The method is even more interesting when we take a signal in which the period changes. In FIG. 10 an input signal is generated where the period of the grid varies from 2,911 to 3.111 pixels. By suppressing 7 spectral components, we do not have the same result as with our short-time Goertzel transform.

Figure 11:
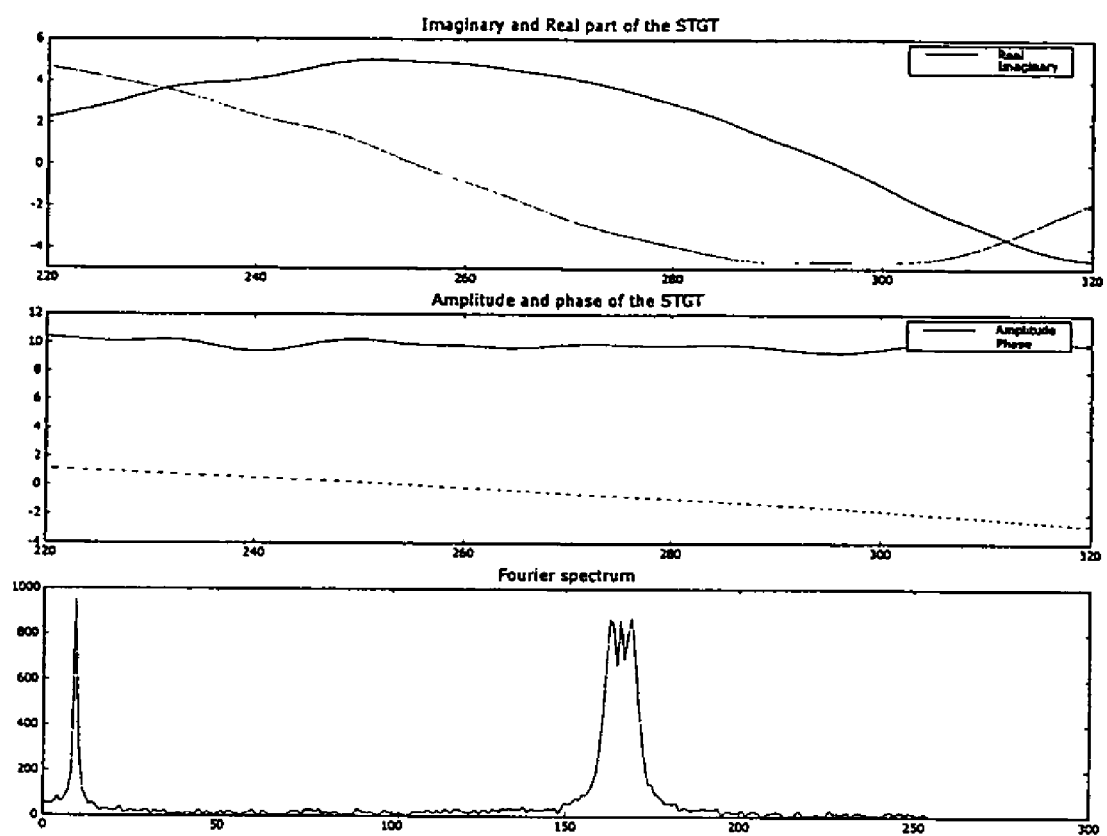
FIG. 11 shows the result of the short-time Goertzel transform of the input signal of FIG. 10 and the Fourier transform of the said input signal. The output of the short-time-Goertzel transform is slowly varying.

An alternative to the Goertzel transform is to design a notch filter which has the same filtering characteristics than the short-time Goertzel transform. The Goertzel transform however, has the advantage that high frequency attenuation, spike-detection algorithms, . . . are easier to implement in the Goertzel domain since its output is slowly varying (see FIG. 7 and FIG. 11).

Figure 12:
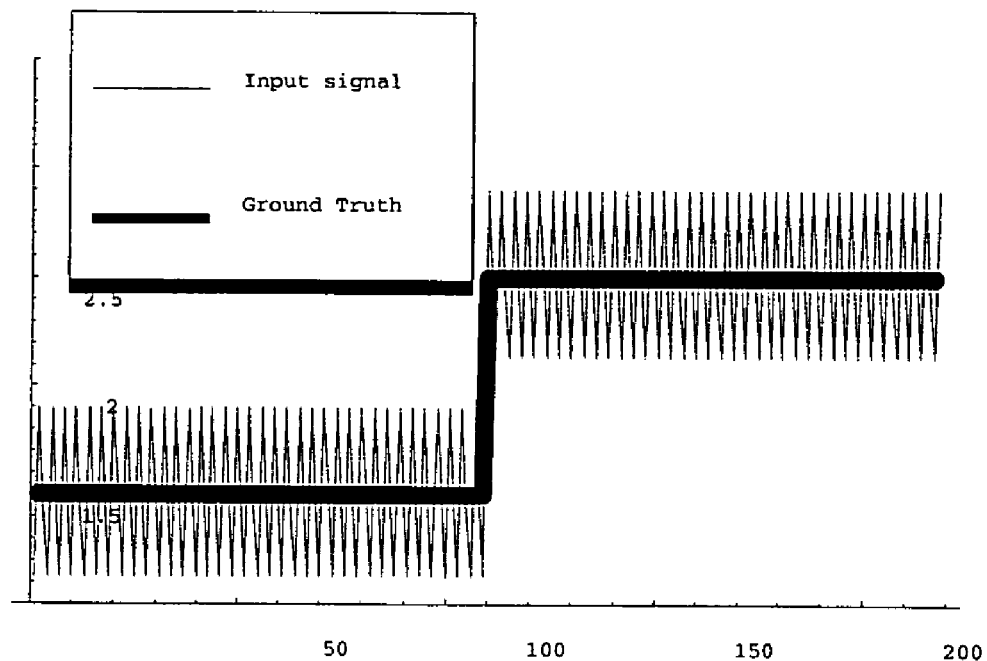
FIG. 12 shows a unit step function disturbed with a linear combination of a sine and cosine function of a given frequency.

The difference between a notch filter and the short time Goertzel transform combined with a non linear filter, in this case a median filter for the amplitude representation of Equation 2, is illustrated on the input signal of FIG. 12. The input signal consists of a unit step disturbed with a signal of a given frequency:

$$s(x)=1.5+\text{UnitStep}(x-128)+0.4\cos(\omega x)+0.2\sin(\omega x)$$

Figure 13:
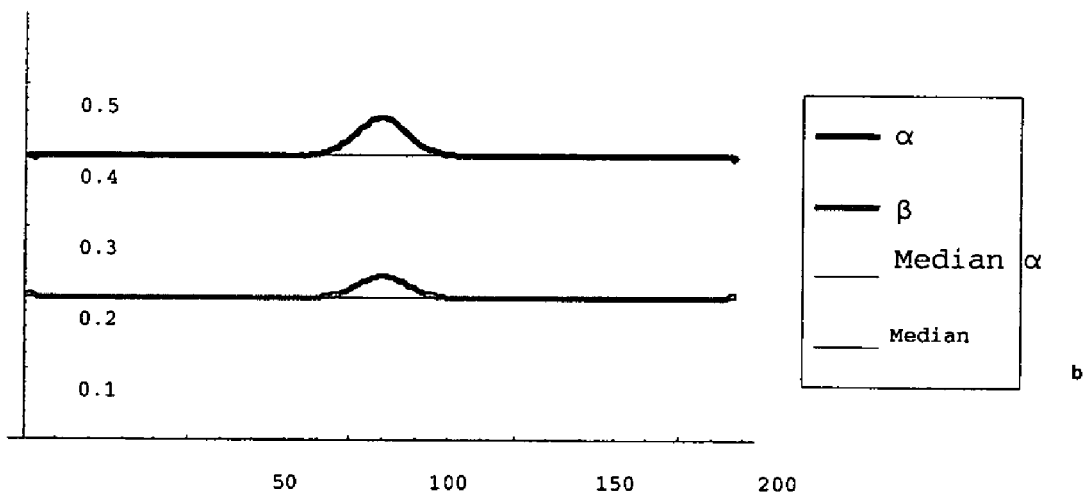
FIG. 13 shows an amplitude representation of the method of the present invention combined with a non linear postprocessing method, a median filter.
Figure 14:
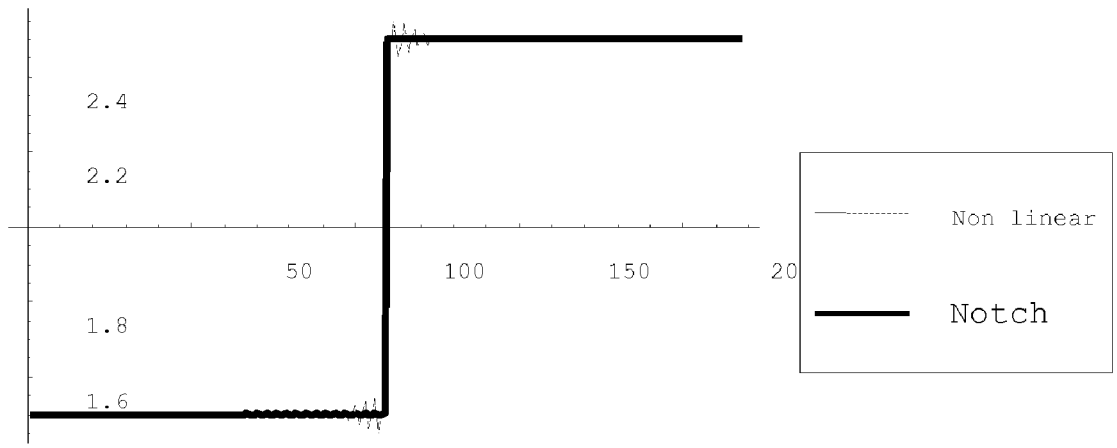
FIG. 14 shows the result of a notch filter for the signal of FIG. 12 and the result of the correction with the method of the present invention, using a non linear postprocessing step presented in FIG. 13.
Figure 14:
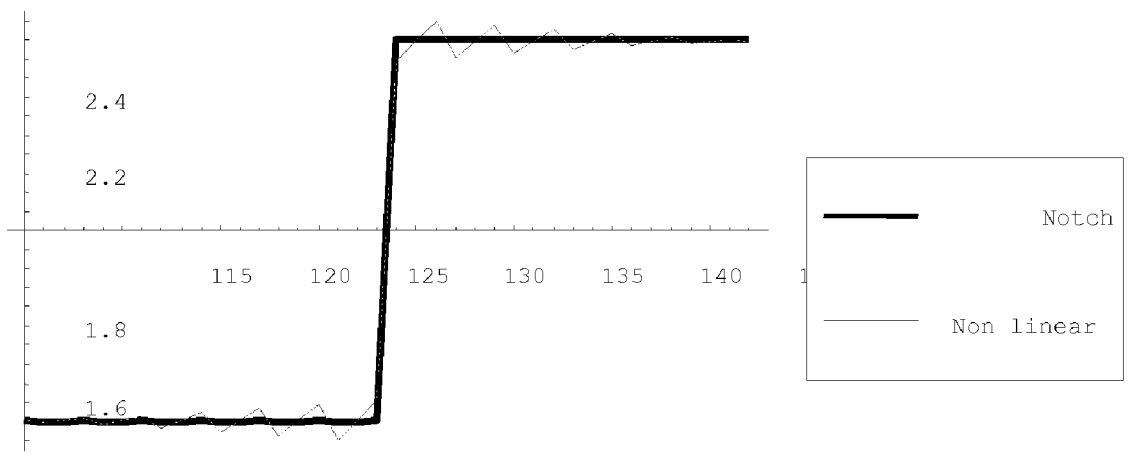

In FIG. 13, the amplitude representation $(\alpha,\beta)$ is shown together with a median filter $(\alpha',\beta')$ version of this amplitude representation. The difference between our non linear short time goertzel transform and a notch filter is given in FIG. 14. We clearly see that at that our filter is capable to almost perfectly reconstruct the step function. The small fluctuations, due to rounding errors, are much smaller than the fluctuations introduced by notch filter.

The invention claimed is:

1. A periodical pattern suppression method wherein a spatial frequency component corresponding to a periodical pattern occurring in an image signal is suppressed, comprising the steps of:
    extracting, via a radiography processing computer, from said image signal the spatial frequency component corresponding to the periodical pattern included therein by applying a transformation to the image signal to transform it into a representation of the spatial frequency component;
    processing, via the radiography processing computer, the representation of the spatial frequency component;
    computing, via the radiography processing computer, the inverse of the transformation on the processed representation of the spatial frequency component; and
    suppressing, via the radiography processing computer, the spatial frequency component occurring in the image signal by eliminating from said image signal the result of said inverse transformation, wherein said transformation is defined by a formula $$\Gamma(y,\omega)=\int w\times(x-y)\times s(x)\times e^{i\omega x}dx$$

wherein $s(x)$ is said image signal, $\omega$ represents a given frequency of the periodical pattern, and
    wherein said processing comprises applying a non-linear high frequency attenuating filter to the representation of the spatial frequency component.

2. A method according to claim 1, wherein the high frequency attenuating filter is implemented with a median filter.

3. A method according to claim 1, where the high frequency attenuating filter is a 2-dimensional filter.

4. A method according to claim 1, wherein the high frequency attenuating filter is a 1-dimensional filter in the same direction as the spatial frequency component.

5. A method according to claim 1, wherein the high frequency attenuation filter is a 1-dimensional filter in the orthogonal direction to the spatial frequency component.

6. A method according to claim 1, wherein the high frequency attenuating filter is a sequence of high frequency attenuating filters including at least one of a 1-dimensional filter and a two-dimensional filter.

7. A method according to claim 1, wherein the filter is applied to the imaginary part of the complex representation.

8. A method according to claim 1, wherein the filter is applied to the real part of the complex representation.

9. A method according to claim 1, wherein the filter is applied to the magnitude of the complex representation.

10. A method according to claim 1, wherein the filter is applied to the phase of the complex representation.

11. A method according to claim 1, wherein the transformation is applied to a filtered version of the image signal.

12. A method according to claim 11, wherein the filtered version of the image signal does not contain the DC component.

13. A method according to claim 11, wherein the filtered version of the image signal only contains frequencies within a certain bandwidth of the frequency to be suppressed.

14. A method according to claim 1, wherein the spatial frequency components are removed which correspond to an image of anti-scatter gridlines in a radiographic image.

15. A non-transitory computer program product adapted to carry out the steps of claim 1 when run on a computer.

16. A non-transitory computer readable carrier medium comprising computer executable program code adapted to carry out the steps of claim 1.

* * * * *